(12) United States Patent
Roth

(10) Patent No.: US 9,240,110 B2
(45) Date of Patent: Jan. 19, 2016

(54) HAPTIC FOOTSWITCH TREADLE

(75) Inventor: Jeremy R. Roth, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 605 days.

(21) Appl. No.: 13/609,472

(22) Filed: Sep. 11, 2012

(65) Prior Publication Data

US 2013/0169412 A1    Jul. 4, 2013

Related U.S. Application Data

(60) Provisional application No. 61/549,321, filed on Oct. 20, 2011.

(51) Int. Cl.
| | | |
|---|---|---|
| *G08B 6/00* | (2006.01) | |
| *H01H 3/14* | (2006.01) | |
| *H01H 21/26* | (2006.01) | |
| *A61B 17/00* | (2006.01) | |
| *H01H 3/00* | (2006.01) | |
| *A61F 9/007* | (2006.01) | |

(52) U.S. Cl.
CPC .. *G08B 6/00* (2013.01); *H01H 3/14* (2013.01); *H01H 21/26* (2013.01); *A61B 2017/00973* (2013.01); *A61F 9/007* (2013.01); *H01H 2003/008* (2013.01); *H01H 2300/014* (2013.01)

(58) Field of Classification Search
CPC ........... A61B 2017/00973; A61B 2017/00977; A61B 2017/00017; A67C 1/0023; G05G 1/38; H01H 3/14; H01H 21/26; H01H 2003/008; H01H 2300/014; A61F 9/007; A61C 1/0023; G08B 6/00

See application file for complete search history.

(56) References Cited

U.S. PATENT DOCUMENTS

| | | | |
|---|---|---|---|
| 5,091,656 A | 2/1992 | Gahn | |
| 5,554,894 A * | 9/1996 | Sepielli | 307/119 |
| 5,635,777 A | 6/1997 | Telymonde et al. | |
| 6,422,941 B1 * | 7/2002 | Thorner et al. | 463/30 |
| 6,862,951 B2 | 3/2005 | Peterson et al. | |
| 6,962,581 B2 | 11/2005 | Thoe | |
| 7,019,234 B1 | 3/2006 | Mezhinsky et al. | |
| 7,084,364 B2 | 8/2006 | Mezhinsky | |
| 7,185,555 B2 | 3/2007 | Peterson et al. | |
| 7,193,169 B2 | 3/2007 | Mezhinsky et al. | |
| 7,381,917 B2 | 6/2008 | Dacquay et al. | |
| 7,602,384 B2 | 10/2009 | Rosenberg et al. | |
| 7,619,171 B2 | 11/2009 | Horvath et al. | |
| 7,626,132 B2 | 12/2009 | Mezhinsky | |
| 7,781,941 B2 | 8/2010 | Horvath et al. | |
| 8,380,126 B1 * | 2/2013 | Ma et al. | 455/41.2 |
| 2003/0073980 A1 | 4/2003 | Finlay et al. | |
| 2004/0036386 A1 | 2/2004 | Olivera | |
| 2004/0106915 A1 | 6/2004 | Thoe | |
| 2005/0039567 A1 | 2/2005 | Peterson et al. | |
| 2006/0145540 A1 | 7/2006 | Mezhinsky | |

(Continued)

*Primary Examiner* — Brian Zimmerman
*Assistant Examiner* — Sara Samson

(57) ABSTRACT

A haptic footswitch treadle for use in microsurgical systems is disclosed. The haptic footswitch treadle includes a haptic surface coupled to a pivotable treadle base and configured to convey vibratory haptic feedback to a surgeon. The haptic footswitch includes a positional sensor coupled to the treadle base and suspension elements and actuators positioned between the haptic surface and the treadle base. The actuators are configured to move the suspension elements and the haptic surface based on command signals generated by haptic software applications in response to data from the positional sensor.

20 Claims, 4 Drawing Sheets

(56) References Cited

U.S. PATENT DOCUMENTS

| | | |
|---|---|---|
| 2007/0149956 A1 | 6/2007 | Liedel et al. |
| 2007/0293844 A1 | 12/2007 | Nazarifar et al. |
| 2008/0062145 A1 | 3/2008 | Shahoian et al. |
| 2008/0243105 A1 | 10/2008 | Horvath |
| 2009/0005789 A1 | 1/2009 | Charles |
| 2010/0198200 A1 | 8/2010 | Horvath |
| 2010/0325931 A1* | 12/2010 | Rosenberg .................. 42/1.08 |
| 2011/0106068 A1 | 5/2011 | Horvath et al. |

* cited by examiner

HAPTIC FOOTSWITCH TREADLE

This application claims priority to U.S. Provisional Application No. 61/549,321 filed Oct. 20, 2011 which is hereby fully incorporated herein by reference.

BACKGROUND

Various footswitches are used to control microsurgical systems, and particularly ophthalmic microsurgical systems. During ophthalmic surgery, a surgeon views the patient's eye through an operating microscope while operating the system with both hands. To control the microsurgical system and its associated handpieces during the surgical procedure, the surgeon must either instruct another healthcare professional how to alter the machine settings on the surgical system, or use a footswitch to change the settings. When possible, many surgeons prefer to use the footswitch to alter the machine settings on the surgical system, eliminating or reducing the need to rely on another healthcare professional to adjust the system settings throughout the surgical procedure.

The footswitches typically have a foot pedal or foot treadle that is capable of movement by the surgeon in a given range of motion to provide linear control of the functions of the surgical system or an associated handpiece. This range of motion is typically segregated into several areas, each of which controls a different surgical mode or surgical function. As the treadle progresses from one position to another, the surgeon may be alerted to the shift in position by increased resistance or haptic feedback against his or her foot that allows him to tactilely distinguish various conditions of the microsurgical system without shifting his attention from the surgical field. In the footswitches supplying haptic feedback, the entire treadle is vibrated or moved in some other fashion to tactilely indicate to the surgeon the particular position of the treadle, and therefore the particular surgical mode, for example. Therefore, these footswitches often require a significant amount of power and/or large actuators to move the treadle to provide the haptic feedback.

Accordingly, there exists a need for an improved surgical footswitch supplying haptic feedback. The system and methods disclosed herein overcome one or more of the deficiencies of the prior art.

SUMMARY

This disclosure relates generally to a haptic footswitch for use during a surgical procedure, and in particular to a haptic footswitch for communication with a health care provider during an ophthalmic using an ophthalmic microsurgical system.

In an exemplary embodiment, a haptic footswitch for communication with a health care provider using an ophthalmic microsurgical system comprises a body, a treadle, at least one suspension element, and at least one actuator. The treadle may be configured to rotate relative to the body, and the treadle may include a haptic surface and a treadle base, wherein the treadle base is pivotably coupled to the body. The at least one suspension element may couple the treadle base and the haptic surface a distance apart from each other, wherein movement of the suspension element in a first direction moves the haptic surface in the first direction. The at least one actuator may be actuatable to displace the haptic surface relative to the treadle base in a manner providing haptic feedback to the health care provider.

In another exemplary embodiment, an ophthalmic microsurgical system may comprise a footswitch and a handpiece. The footswitch may comprise a body, a treadle, at least one suspension element, at least one actuator, and a sensor. The treadle may be configured to rotate relative to the body, and comprise a haptic surface and a treadle base. The treadle base may be pivotably coupled to the body, wherein the haptic surface is supported by and spaced a distance apart from the treadle base and is displaceable relative to the treadle base. The at least one suspension element may be coupled to the haptic surface and separate the haptic surface and the treadle base. The at least one actuator may be actuatable to displace the haptic surface relative to the treadle base in a manner providing haptic feedback to the health care provider, wherein movement of the actuator causes movement of the haptic surface relative to the treadle base. The sensor may be configured to sense the rotational position of the treadle relative to the body and convey data representative of the position of the treadle. The handpiece may have a plurality of functions that may be selectively activated based on the rotational position of the treadle.

In another exemplary embodiment, a method of providing haptic feedback by a footswitch to a health care provider during a surgical procedure may comprise detecting a position of a treadle relative to a body of the footswitch with a sensor, wherein the detected position corresponds to surgical mode controllable by the footswitch, generating an actuator command signal based on the detected position of the treadle, wherein the actuator command signal has a haptic feedback profile corresponding to the detected position, and actuating an actuator in accordance with the actuator command signal to displace a haptic surface of the treadle relative to a treadle base of the treadle to signal to the healthcare provider that the treadle is in the detected position.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
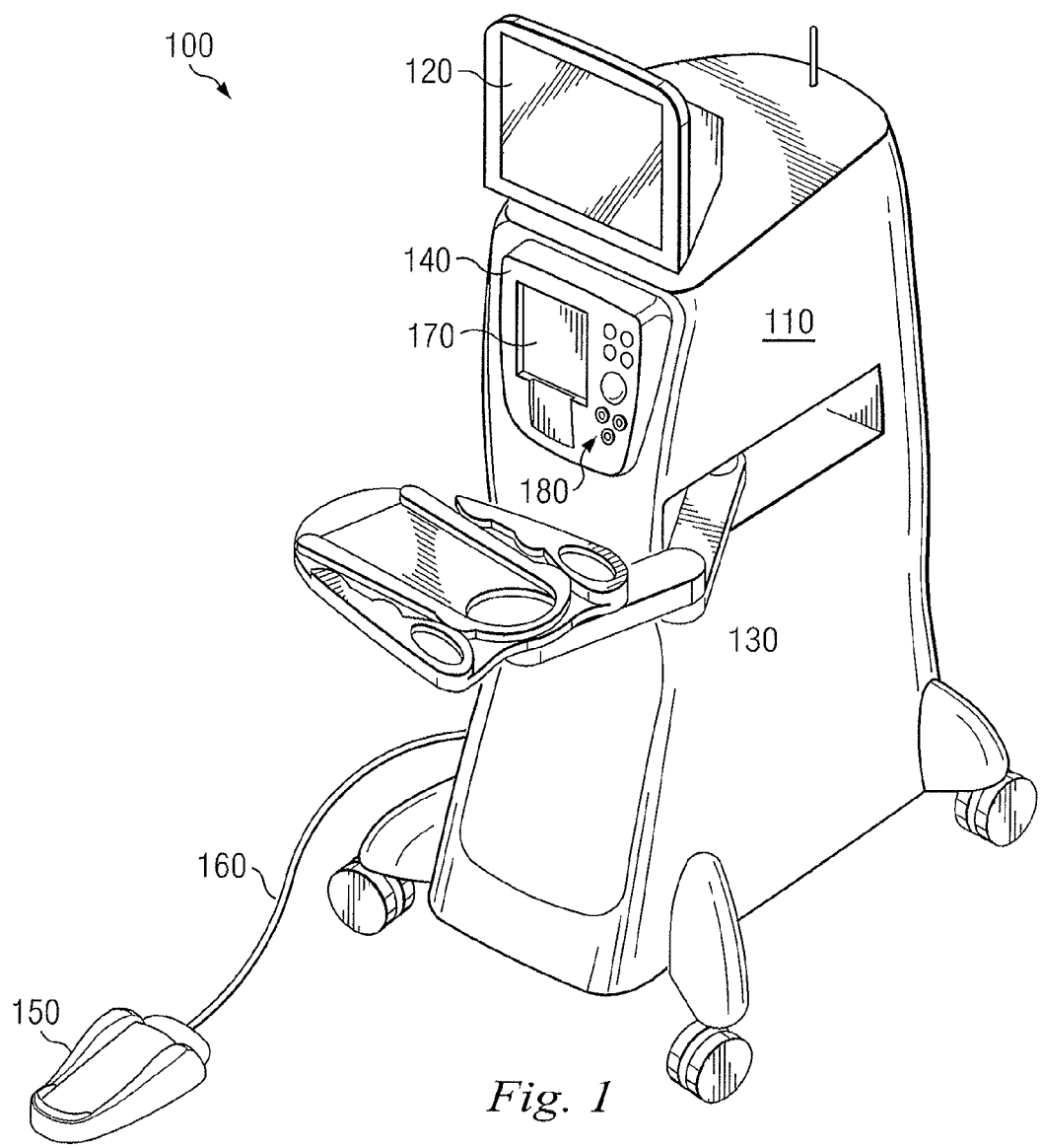
FIG. 1 is an illustration of a perspective view of a microsurgical system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to footswitches supplying haptic feedback used in the operation of microsurgical systems. In some instances, embodiments of the present disclosure are configured to be part of an ophthalmic surgical system. Instead of supplying haptic feedback through movement of the entire treadle, the footswitches disclosed herein supply haptic feedback to the user through the isolated movement of an elevated surface portion of a pivotable foot treadle relative to a base portion of the treadle. Therefore, the footswitches disclosed herein may utilize lower power actuation to provide haptic feedback than conventional footswitches, thereby allowing for wirelessly operated, battery powered haptic footswitches. Additionally, the haptic feedback may comprise various distinguishable sensations to communicate different treadle positions and system states to the user.

FIG. 1 illustrates a microsurgical system 100 according to one embodiment of the present disclosure. Though the microsurgical system 100 shown in FIG. 1 is an ophthalmic microsurgical system, the microsurgical system may be any microsurgical system, including a system for performing otic, nasal, throat, maxillofacial, or other surgeries. The system 100 is capable of providing ultrasound power, irrigation fluid, and aspiration vacuum to an ultrasonic handpiece in an anterior segment ophthalmic surgical procedure. The system 100 may also be capable of providing pneumatic drive pressure and aspiration vacuum to a vitrectomy probe and irrigation fluid to an irrigation cannula in a posterior segment ophthalmic surgical procedure.

In the pictured embodiment, the system 100 includes a body 110, a graphic user interface 120 attached to the body 110, a footswitch interface controller (FIC) 130 disposed within the body 110, a control console 140 disposed on a surface of the body 110, and a footswitch 150 connected to the FIC 130 via a bi-directional bus or cable 160. In some embodiments, the graphic user interface 120 has a liquid crystal display (LCD) with touch screen capability. In other embodiments, the graphic user interface may include any of a variety of display devices, including by way of non-limiting example, LED displays, CRT's, and flat panel screens. The graphic user interface may include additional input devices or systems, including by way of non-limiting example, a keyboard, a mouse, a joystick, dials, buttons, among other input devices. The control console 140 includes a cassette receiving area 170 and a plurality of ports 180. A surgical cassette may be operatively coupled to the system 100 via the cassette receiving area 170 to manage the fluidics of the system 100 in a conventional manner. The bi-directional bus 160 sends signals in either direction between the FIC 130 and the footswitch 150, and may be used to transmit power to the footswitch 150. In some embodiments, the FIC 130 and the footswitch 150 communicate through a wireless connection.

During ophthalmic surgery, a series of handpieces may be coupled to the system 100, typically via conventional flexible plastic tubing fluidly coupled with the surgical cassette and/or electric cabling to operatively connect to the system 100 through one or more of the ports 180. Some exemplary handpieces that are utilized in anterior segment ophthalmic surgery include, for example, an irrigation handpiece, an irrigation/aspiration handpiece, an ultrasonic handpiece, and a diathermy handpiece. One type of exemplary ultrasonic handpiece is a phacoemulsification handpiece. Exemplary handpieces that are utilized in posterior segment ophthalmic surgery include, by way of non-limiting example, an extrusion handpiece, an infusion cannula, a vitrectomy probe, microsurgical scissors, and a diathermy handpiece.

The system 100 may include a microprocessor, random access memory (RAM), read only memory (ROM), input/output circuitry such as the bus 160, an audio output device, and other components of microsurgical systems well known to those in the art. A variety of peripheral devices may also be coupled to the system 100, such as storage devices (hard disk drive, CD ROM drive, etc.), printers, and other input/output devices.

Figure 2:
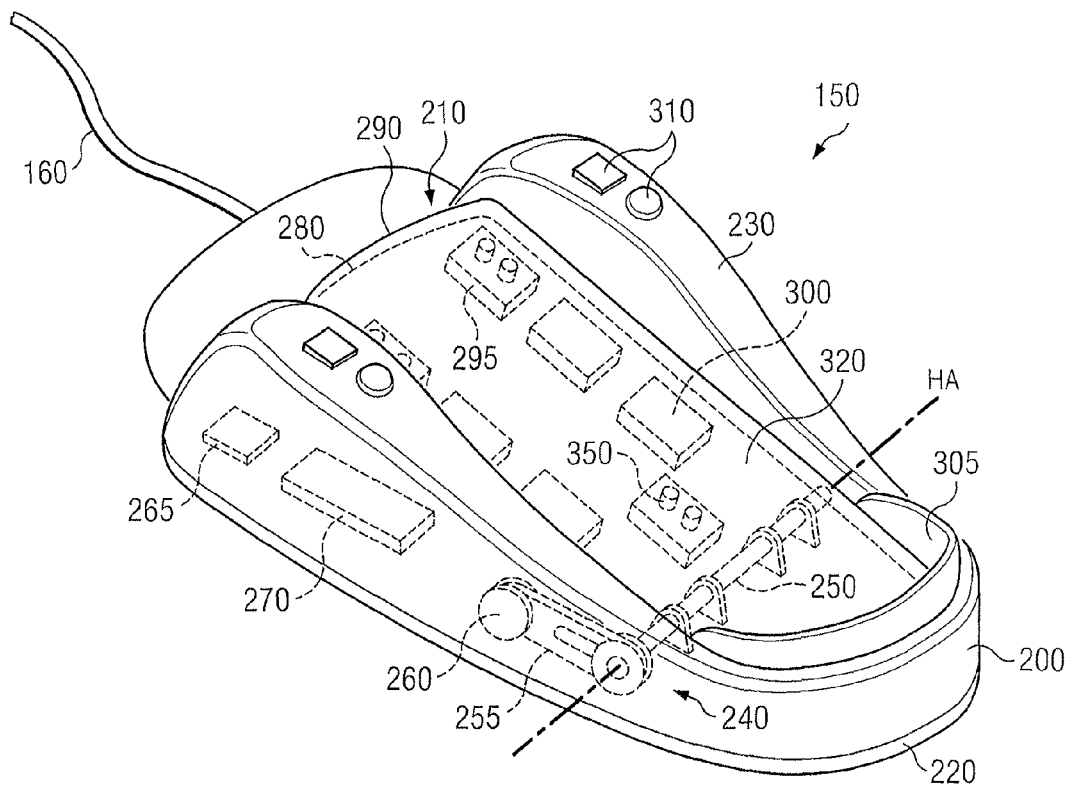
FIG. 2 is an illustration of a partially transparent, perspective view of the footswitch illustrated in FIG. 1 according to one embodiment of the present disclosure.

FIG. 2 illustrates the footswitch 150 used to control various operational modes and functions of the microsurgical system 100 according to one embodiment of the present disclosure. The footswitch 150 includes a body 200 surrounding a foot pedal or treadle 210. The body 200 is attached to a base 220 that supports the footswitch 150 on the operating room floor. The body 200 includes side walls 230, which form the raised sides of the body 200. The body 200 houses a drive train 240, which includes a shaft 250 and a gear assembly 255, and a sensor 260. The body may house a microprocessor 270, which may be in communication with the sensor 260 and/or the FIC 130. The treadle 210 is positioned between the side walls 230 and is coupled to the body 200 via the shaft 250, which may be coupled to the sensor 260 via the gear assembly 255. Unlike conventional treadles comprising one integral structure, the treadle 210 includes a treadle base 280 and a haptic surface 290. As will be described below, the haptic surface 290 is supported above the treadle base 280, thereby allowing the footswitch 150 to provide haptic feedback by moving the isolated haptic surface 290 independent of or relative to the treadle base 280. Support members 295 and actuators 300 are disposed between and maintain the isolation of the treadle base 280 and the haptic surface 290. A heel cup 305 may be attached to the treadle 210. The body 200, the treadle 210, the base 220, and the heel cup 305 may be made from any suitable material, including, by way of non-limiting example, stainless steel, titanium, and/or plastic.

In some embodiments, the side walls 230 are in a fixed position relative to the treadle 210. In other embodiments, the side walls 230 may be adjusted inwardly or outwardly to decrease or increase the space available between the side walls 230 to accommodate for variations in the width of a user foot. In the pictured embodiment, the side walls 230 include switches or buttons 310 that may be used by the surgeon to change various operating characteristics of the system 100.

The cable 160 extends from and connects the footswitch 150 to the body 110 of the system 100 and provides electrical communication therebetween and provides power to the footswitch. In one embodiment, the footswitch is a wireless footswitch and contains its own powersource 265. The powersource may be a rechargeable battery, such as a lithium ion or lithium polymer battery, although other types of batteries may be employed. In addition, any other type of power cell is appropriate for power source 205.

In the pictured embodiment, the body 200 houses the microprocessor 270 to allow for efficient communication with other system components, such as the sensor 260 and/or the FIC 130. The microprocessor 270 may include one microprocessor chip, multiple processors and/or co-processor chips, and/or digital signal processor capability. In other embodiments, the body may lack a microprocessor and therefore, processing and control may be entirely performed on the FIC 130 of the microsurgical system 100 illustrated in FIG. 1. In wireless embodiments, communication between the FIC 130 and the microprocessor 270 may occur through a series of transmitting and receiving components onboard the footswitch 150 and within the body 110.

The treadle base 280 is shaped and configured to anchor the treadle 210 to the body 200 via the shaft 250. The shaft 250 is a straight, rod-like structure extending through the sidewalls 230 and the treadle base 280 such that the treadle 210 is pivotably disposed between the side walls 230. In FIG. 2, the treadle 210 is shown in a resting condition, with the treadle 210 positioned in alignment with a neutral or resting plane. The treadle 210 is tiltable or pivotable with respect to the body 200 around an axis HA extending through the shaft 240. The axis HA is substantially perpendicular to a longitudinal axis of the footswitch 150.

Figure 3:
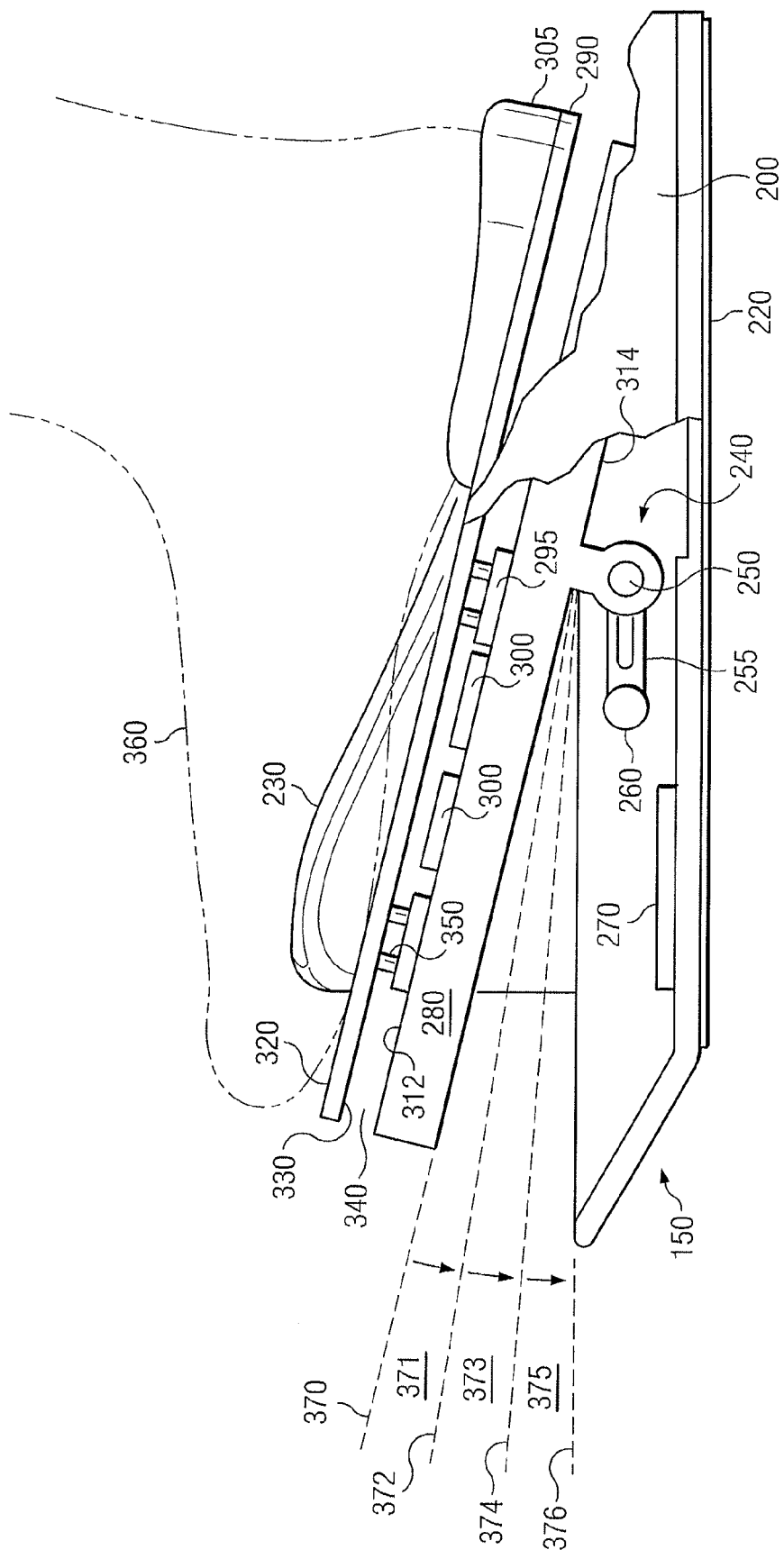
FIG. 3 is an illustration of a side, partially cross-sectional view of the footswitch illustrated in FIG. 2 in a fully undepressed position according to one embodiment of the present disclosure.

As shown in FIG. 3, the treadle base 280 includes a superior face 312 and an inferior face 314. The haptic surface 290 is shaped and configured as a continuous, substantially planar surface overlying and spaced apart from the superior face 312 of the treadle base 290. In the embodiment pictured in FIGS. 2 and 3, the two-dimensional surface geometry of the haptic surface 290 mimics the two dimensional surface geometry of the treadle base 280. In some embodiments, the surface area of the haptic surface may be smaller or larger than that of the treadle base 280. In the pictured embodiment, the haptic surface 290 is configured to be thinner than and possess less mass than the treadle base 290.

As shown in FIG. 3, the haptic surface 290 includes a superior face 320 and an inferior face 330. The haptic surface 290 is positioned over the treadle base 290 such that a gap or space 340 exists between the inferior face 330 of the haptic surface 290 and the superior face 312 of the treadle base 280. The gap 340 is sized to accommodate the support members 295 and the actuators 300. In the pictured embodiment, the gap 340 has a uniform width along the length and width of the treadle 210 (i.e., the space between the haptic surface 290 and the treadle base 280 is uniform). In other embodiments, the gap between the haptic surface 290 and the treadle base 280 may vary along the length and/or width of the treadle 210. The haptic surface 290 may be formed of any of a variety of rigid or substantially rigid materials.

In some embodiments, the haptic surface may comprise a substantially stiff base material forming the inferior face coupled to a more flexible surface material forming the superior face. In some embodiments, the superior surface of the haptic surface may be textured to provide frictional engagement with the surgeon's foot.

The support members 295 and the actuators 300 are attached to the superior surface 312 of the treadle base 280 and reside within the gap 340. The support members may be attached to the treadle base 280 by any of a variety of known methods, including by way of non-limiting example, adhesive, welding, and/or mechanical fasteners. Returning to FIG. 2, the support members 295 compliantly couple the haptic surface 290 to the treadle base 280. In particular, the support members 295 include suspension elements 350 that extend between and, in some embodiments, compliantly couple together the support members 295 and the inferior face 330 of the haptic surface 290. The suspension elements 350 provide, among other things, a stop that prevents the haptic surface 290 from contacting the superior face 312 of the treadle base 280 when the surgeon's foot presses on the haptic surface 290. The suspension elements 350 may be made of any of a number of rigid materials or compliant materials with linear or non-linear spring rates such that they prevent the haptic surface 290 from travelling toward the treadle base 280 when the haptic surface 290 is pressed upon by the surgeon.

By way of non-limiting example, the suspension elements 350 may be of various types, including coil springs, leaf springs, roller bearings, and/or other types of suspensions. In some embodiments, the suspension elements may be integral extensions of the support members. In other embodiments, the suspension elements may be separate components that are coupled to the support members by any of a variety of known methods, including by way of non-limiting example, adhesive, welding, and/or mechanical fasteners.

Activation of the actuators 300 may generate multi-directional movement of the suspension elements 350 and the haptic surface 290 relative to the treadle base 280. Because the actuators 300 and suspension elements 350 act on and move only the haptic surface 290 to provide haptic feedback, as opposed to the entire treadle 210, the actuators 300 and the suspension elements 350 move less mass than conventional footswitches that move an entire treadle to provide haptic feedback. Therefore, the actuators 300 and the suspension elements 350 require less power and may be smaller than those found in conventional haptic footswitches because the actuators 300 and the suspension elements 350 are moving less mass. This characteristic, in at least one example, permits the footswitch 150 to be battery powered, enabling the footswitch to be operated in a wireless manner as discussed above.

In the pictured embodiment, the actuators 300 are horizontally attached to the superior surface 312 of the treadle base 280 and reside within the gap 340. The actuators 300 may be coupled to the suspension elements 350 by any mechanism that allow lateral movement of the suspension elements 350 in any direction. In alternative embodiments, the actuators may be mounted vertically to the treadle base 280 and coupled to the suspension elements to provide vertical movement of the haptic surface 290 (i.e., elevation and depression of the haptic surface 290). The actuators 300 may be attached to the treadle base 280 by any of a variety of known methods, including by way of non-limiting example, adhesive, welding, and/or mechanical fasteners.

The actuators may be any of a number of actuator types, including, without limitation, solenoids, linear resonance actuators, voice coil actuators, eccentric rotary mass actuators, E-core type actuators, moving magnet actuators, piezoelectric film, or other types of actuators capable of causing the motion of the haptic surface 290. For example, the actuators may be a linear actuator such as the commercially available "Immersion A100" haptic actuator designed by Immersion Corporation. The actuators 300 will be described in further detail with respect to FIGS. 5 and 6.

In the pictured embodiment, the footswitch 150 includes three support members 295, six suspension elements 350, and four actuators 300 arranged in a symmetrical fashion. However, other numbers, relative sizes, and configurations of support members, suspension members, and actuators are contemplated. In particular, nonsymmetrical configurations of support members, suspension members, and actuators are contemplated.

The heel cup 305, which may be attached to the treadle 210, secures the surgeon's heel on the treadle 210 and guards against inadvertent slippage off the treadle 210. In the pictured embodiment, the heel cup 305 is in a fixed position relative to the treadle 210. In other embodiments, the heel cup 305 may be adjusted along the longitudinal axis of the treadle 210 to increase or decrease the space available to accommodate for variations in the length of a user foot. In the pictured embodiment, the treadle 210 and the heel cup 305 are coupled such that the treadle 210 and the heel cup 305 rotate in unison about the shaft 250. The heel cup 305 may be fixed relative to the treadle base 29 or the haptic surface 290, depending upon the embodiment. In alternative embodiments, the footswitch 150 may be constructed so that only the treadle 210, and not the heel cup 305, rotates about the shaft 250.

FIG. 3 illustrates a surgeon's foot 360 resting on the footswitch 150 while the footswitch 150 is in a fully undepressed position according to one embodiment of the present disclosure. The treadle 210 may be moved by a surgeon in a given range of motion to change operational mode and provide proportional control to various operational functions of the microsurgical system 100. In some embodiments, the treadle 210 may rotate or pivot from about zero to about ten degrees about the shaft 250. Other ranges of rotation are contemplated. This range of motion is typically segregated into several positions, each of which controls a different surgical mode. Neighboring positions frame or bookend distinct areas that provide proportional control over the functions of particular operational mode defined by each particular position.

By way of nonlimiting example, depending on the operating mode of the system 100, the treadle 210 may be used to provide proportional control, stepped control, or ON-OFF powering of vitrectomy probe cut rate, vitrectomy probe aspiration vacuum, ultrasound handpiece power, and/or ultrasound handpiece aspiration flow rate. As the treadle 210 rotates about the shaft 250 to progress from one position to another, the surgeon may be tactilely alerted to the shift in position, and consequently the change in operational mode or function, by haptic feedback from the haptic surface 290 against his or her foot. For example, for an exemplary phacoemulsification handpiece operatively coupled to system 100, according to one embodiment of the present disclosure, keeping the treadle 210 in a first position 370 may provide no active surgical operations. Moving the treadle 210 through a first area 371 may provide a fixed amount of irrigation flow to a handpiece. Moving the treadle 210 into a second position 372 may provide fixed irrigation flow and activate control of aspiration flow into the handpiece. Moving the treadle 210 through the second area 373 may provide fixed irrigation flow and proportional, linear control of aspiration flow. Moving the treadle 210 into a third position 374 may activate control of ultrasound power to the handpiece. Moving the treadle 210 through the third area 375 towards a fourth, fully depressed position 376 may provide fixed irrigation flow, proportional, linear control of aspiration flow, and proportional, linear control of ultrasound power to the handpiece. In alternative embodiments, different numbers of positions and areas, as well as different surgical modes, may be assigned for different microsurgical systems other than system 100 and/or different handpieces operatively coupled to the system 100. In some embodiments, the number of positions and areas and the corresponding surgical modes may be set by the surgeon using the control console 140 of the system 100.

As described above and shown in FIG. 3, the treadle 210 and the heel cup 305 are pivotally coupled to the body 200 by the shaft 250 of the footswitch 150. As illustrated in FIG. 3, the surgeon's foot 360 may depress the treadle 210 from the fully undepressed first position 370 to the fully depressed fourth position 376. Each of the positions is typically separated by a relatively small range of treadle travel in which the surgeon may feel haptic feedback against his or her foot 360 as it presses the treadle through the distinct areas into new positions. These small ranges of treadle travel separating the areas are typically referred to as detents. In various embodiments, the treadle may be depressed through any of a number of detents, which may be spaced equally or unequally from each other. As the surgeon's foot 360 depresses the treadle 210, the haptic surface 290 and the treadle base 280 remain in a substantially fixed distance apart and rotate in unison about the shaft 250.

Rotation of the treadle 210 about the shaft 250 is detected by the sensor 260. As the shaft 250 rotates, the gear assembly of the drivetrain 240 operates to rotate the sensor 260 such that the sensor 260 may sense the angle of rotation of the shaft 250 (and thereby sense the rotational displacement of the treadle 210). The drive ratio between the drivetrain 240 and the sensor 260 may be increased to amplify the rotational movement of the treadle 210 with respect to the sensor 260 to achieve greater positional accuracy. In the pictured embodiment, the sensor 260 is an optical encoder. In alternative embodiments, the sensor 260 may be any suitable device, including by way of non-limiting example, a mechanical switch, potentiometer, an optical sensor, a rotary encoder, a digital measurement system, a strain gauge, and/or other type of positional sensor. In various embodiments, relative or absolute positional sensors may be used.

The treadle 210, the drivetrain 240, and the sensor 260 cooperate with electronic components of the microsurgical system 100 and/or the footswitch 150 to activate the actuators 300 to provide haptic feedback to the surgeon through the haptic surface 290. The sensor 260 detects the rotational displacement and position of the treadle 210 and communicates data representative of the position of the treadle 210 to the electronic components of the system 100 and/or footswitch 150. The sensor 260 may communicate data corresponding to the sensed position of the treadle 210 to the microprocessor 270 of the footswitch 150, or may include the circuitry necessary to communicate such data directly to the FIC 130 of the microsurgical system 100 illustrated in FIG. 1. The microprocessor 270 may report positional data to the FIC 130 of the microsurgical system 100 and/or may process command signals from the FIC 130 to control the actuators 300 and the haptic feedback mechanism of the haptic surface 290. In alternative embodiments, the microprocessor 270 may independently issue command signals to control the actuators 300 and the haptic feedback mechanism of the haptic surface 290. In alternative embodiments, the FIC 130 may independently issue command signals to control the actuators 300 and the haptic feedback mechanism of the haptic surface 290.

The FIC 130 and/or the microprocessor 270 may include embedded software applications necessary to control the haptic feedback response mechanism of the footswitch 150. Such software applications contain haptic feedback programs designed to read information from the control console 140 and the sensor 260 to create a distinct haptic effect for a given event, whether the event is a footswitch-mediated transition through surgical modes or a surgical occurrence at the handpiece. The software application may generate distinguishable haptic sensations to tactilely convey various operating conditions and modes to the surgeon without requiring the surgeon to shift his attention from the surgical field. For example, the software application may generate haptic effects having varying amplitude, shape, duration, and frequency to convey different surgical conditions or operational modes of the system 100. In some embodiments, the software applications may provide for auditory tone notification of various events. An exemplary software application for use in some embodiments of the present disclosure is the TouchSense Player technology from Immersion Corporation. Command signals generated by the software applications may include the type of haptic sensation and parameters describing various characteristics of the commanded haptic sensation transmitted to the haptic surface 290, such as amplification, duration, frequency, shape, and amplitude.

Figure 4:
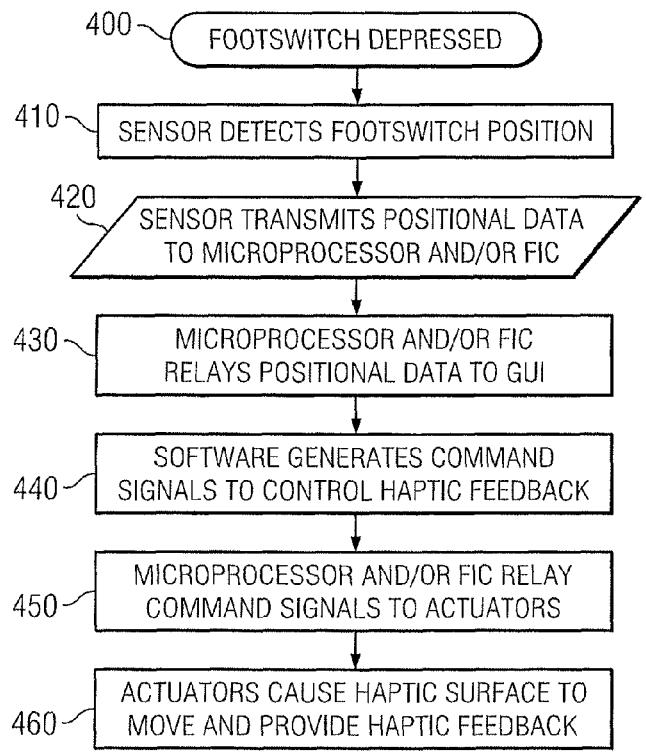
FIG. 4 is a flow diagram illustrating the haptic feedback process between the footswitch and the microsurgical system illustrated in FIG. 1 according to one embodiment of the present disclosure.

FIG. 4 is a flow diagram illustrating an exemplary haptic feedback process between the footswitch 150 and the microsurgical system 100 according to one embodiment of the present disclosure. Initially, at step 400, the surgeon depresses the treadle 210 to a particular position, causing the simultaneous rotation of the drivetrain 240, including the shaft 250 and the gear assembly 255.

At step 410, the rotation of the drivetrain 240 causes the simultaneous rotation of the sensor 260, which detects the rotational displacement and/or position of the treadle 210 relative to the body 200.

At step 420, the sensor 260 transmits the data corresponding to the rotational displacement and/or position of the treadle 210 relative to the body 200 to the microprocessor 270 and/or the FIC 130.

At step 430, the microprocessor 270 and/or the FIC 130 relays the positional data received from the sensor 260 to the guided user interface (GUI) 120, which displays the positional data and corresponding operational mode of the footswitch 150.

At step 440, the microprocessor 270 and/or the FIC 130 utilize the embedded software applications to generate command signals based on the positional data received from the sensor 260 to control the actuators 300 and the haptic feedback mechanism of the haptic surface 290. In the embodiment pictured in FIGS. 2 and 3, the footswitch 150 includes a microprocessor 270, which includes software applications designed to generate command signals based on the positional data received from the sensor 260 to control the actuators 300 and the haptic feedback mechanism of the haptic surface 290. In some embodiments, the microprocessor 270 contains the software applications necessary to control actuators 300 and the haptic feedback mechanism of the footswitch 150 independently of the FIC 130. In such embodiments, the microprocessor 270 may issue command signals based on the data received from the sensor 260 directly to the actuators 300 to trigger the haptic feedback of the haptic surface 290. In other embodiments, the microprocessor 270 relays the positional data received from the sensor 260 to the FIC 130 and receives command signals from the FIC 130, which contains the software applications necessary to generate the appropriate command signals. In some embodiments, the FIC 130 contains the software applications and circuitry necessary to receive the data from the sensor 260 and control the actuators 300 and the haptic feedback mechanism of the footswitch 150 independently of the microprocessor 270. Such embodiments may lack a microprocessor 270. In other embodiments, the FIC 130 may contain the software applications necessary to issue command signals, but needs to issue those command signals to the microprocessor 270 over the bus 160 (shown in FIG. 1) to activate the actuators 270 and the haptic feedback mechanism of the footswitch 150.

At step 450, the microprocessor 270 and/or the FIC 130 relay the command signals to the actuators 300 to initiate the haptic feedback of the haptic surface 290.

At step 460, the actuators 300 transmit forces to the haptic surface 290 in response to command signals received from the microprocessor 270 and/or the FIC 130. More specifically, the actuators 300 activate or move the support members 295 and/or the suspension elements 350 to provide haptic feedback to the surgeon through movement of the haptic surface 290.

Figure 5:
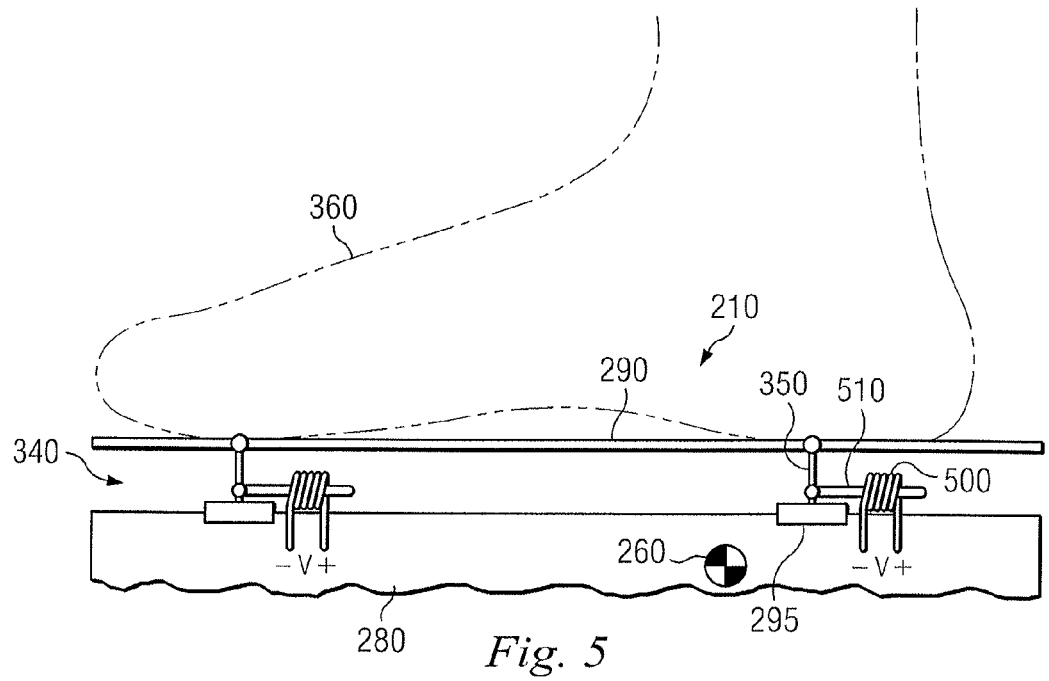
FIG. 5 is a schematic illustration of a side view of the treadle of the footswitch illustrated in FIGS. 2 and 3 in an inactive condition according to one embodiment of the present disclosure.
Figure 6:
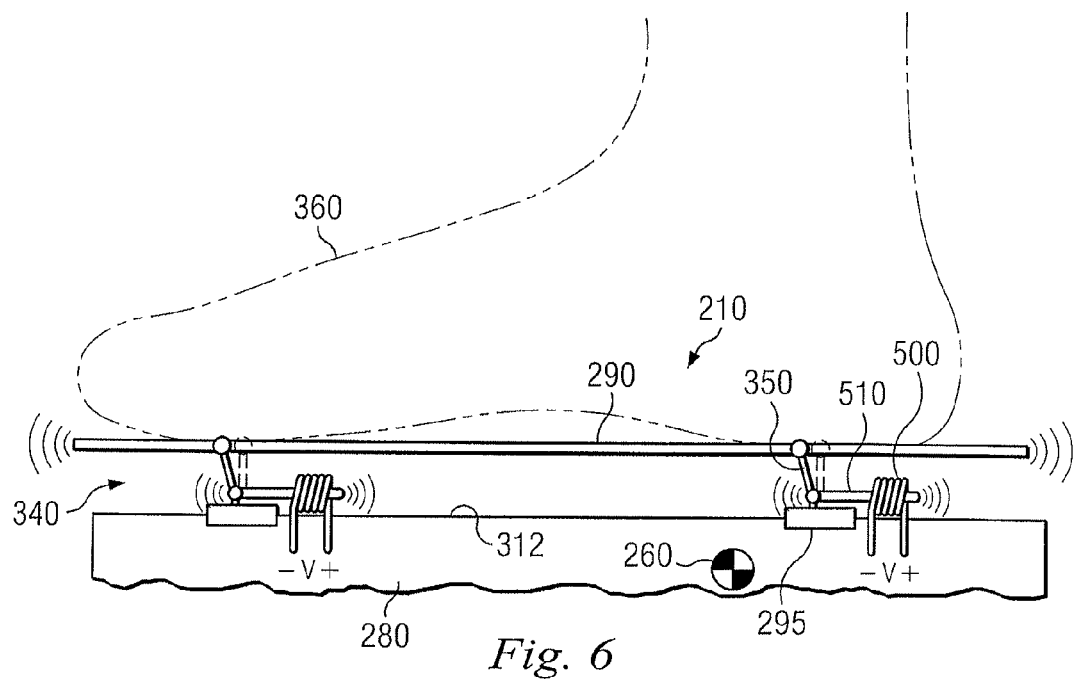
FIG. 6 is a schematic illustration of a side view of the treadle illustrated in FIG. 5 in an active condition according to one embodiment of the present disclosure.

FIGS. 5 and 6 are schematic illustrations of a side view of the treadle 210 according to one embodiment of the present disclosure. In the larger environment of the treadle 210 pictured in FIGS. 5 and 6, the footswitch 150 includes a microprocessor 270, which includes software applications designed to generate command signals based on the positional data received from the sensor 260 to control the actuators 300 and the haptic feedback mechanism of the haptic surface 290.

FIG. 5 illustrates the treadle 210, including the treadle base 280 and the haptic surface 290 separated by the gap 340, in an inactive, stationary condition. As described above in relation to FIG. 2, the actuators 300 are disposed on the treadle base 280 and are coupled to the suspension elements 350 and/or the support members 295 such that activation of the actuators 300 may impart mechanical force to the suspension elements 350. The actuators 300 pictured in FIGS. 5 and 6 are haptic solenoids, which comprise electromagnetically inductive coils 500 and moveable steel or iron cores 510. The coils 500 are wound around the cores 510 such that the cores 510 may move in and out of the center of the coils 500, altering the coils' inductance and thereby becoming electromagnets. The cores 510 are coupled to the suspension elements 350 and impart mechanical force to the suspension elements 350 when the actuators 300 are activated.

FIG. 6 is a schematic illustration of a side view of the treadle 210 in an active condition according to one embodiment of the present disclosure. When the command signals activate the actuators 300, which may be either voltage or current controlled, the actuators 300 may generate multi-directional movement of the suspension elements 350 and the haptic surface 290 relative to the treadle base 280. In the pictured embodiment, when the actuator 300 is activated, the core 510 moves in a reciprocating fashion back-and-forth within the center of the coil 500 along the longitudinal axis of the footswitch 150. Because the core is coupled to the suspension element 350, the reciprocating movement of the core 510 forces the simultaneous and proportional reciprocating movement of the suspension element 350, which causes the simultaneous and proportional reciprocating movement of the haptic surface 290. The reciprocating movement of the haptic surface 290 is felt by the surgeon through his foot 360, alerting him to various surgical conditions and operational modes of the system 100 via vibratory haptic feedback.

The particular characteristics of the vibratory haptic feedback, including amplitude, duration, frequency, and shape, are determined by the command signals sent from the microprocessor 270 or the FIC 130 based on the positional data sensed by the sensor 260. The number and distribution of actuators 300 and suspension elements 350 coupled to the haptic surface 290 may vary the magnitude and strength of the mechanical forces applied to the haptic surface 290. The greater the number of actuators 300 and suspension elements 350 coupled to the haptic surface 290, the greater the magnitude and strength of the mechanical forces applied to the haptic surface 290.

In some embodiments, multiple actuators and suspension elements may be coupled to a particular portion of the haptic surface 290, thereby creating stronger haptic effects in that particular portion of the haptic surface 290. Different magnitudes and localized haptic effects may also be obtained by activating some but not all of the actuators. In alternative embodiments, the actuators and the suspension elements may be positioned or configured to move the haptic surface 290 in any of a variety of ways, including by way of non-limiting example, in a vertical direction perpendicular to the superior surface 312 of the treadle base 280 or in a side-to-side direction in the plane of the surface of the haptic surface 290 and perpendicular to the longitudinal axis of the footswitch 150.

The systems and methods disclosed herein may enable the haptic footswitch to provide haptic feedback using less power than conventional haptic footswitches. By supplying haptic feedback through the treadle surface, which is spaced apart from the treadle base, instead of the entire treadle, the footswitch may utilize smaller actuators and a lower power supply, thus enabling wirelessly operated, battery powered haptic footswitches.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. A haptic footswitch for communication with a health care provider using an ophthalmic microsurgical system, comprising:
    a body;
    a treadle configured to rotate relative to the body, the treadle including a haptic surface and a treadle base, the treadle base pivotably coupled to the body;
    at least one suspension element coupling the treadle base and the haptic surface a distance apart from each other, wherein movement of the suspension element in a first direction moves the haptic surface in the first direction; and
    at least one actuator actuatable to displace the haptic surface relative to the treadle base in a manner providing haptic feedback to the health care provider.

2. The haptic footswitch of claim 1, further comprising a shaft extending through the body and the treadle base in a direction substantially parallel to a horizontal axis of the footswitch, wherein the shaft pivotably couples the treadle base to the body.

3. The haptic footswitch of claim 1, further Comprising:
    a processor; and
    a sensor configured to sense the position of the treadle relative to the body and convey data representative of the position of the treadle to the processor.

4. The haptic footswitch of claim 3, wherein the processor is configured to direct haptic feedback based on the data and configured to activate the at least one actuator.

5. The haptic footswitch of claim 3, wherein the at least one suspension element provides haptic feedback through isolated movement of the haptic surface independent of the treadle base.

6. The haptic footswitch of claim 1, wherein the haptic surface is shaped and configured as a substantially planar surface having an outer geometry substantially the same as the outer geometry of the treadle base.

7. The haptic footswitch of claim 1, wherein the haptic surface possesses less mass than the treadle base.

8. The haptic footswitch of claim 1, wherein the at least one actuator is coupled to the at least one suspension element and configured to move the at least one suspension element in the first direction, thereby moving the haptic surface in the first direction.

9. The haptic footswitch of claim 8, wherein the haptic surface is spaced the distance apart from the treadle base forming a gap between the haptic surface and the treadle base, the at least one suspension element and the at least one actuator are positioned within the gap.

10. The haptic footswitch of claim 1, wherein the at least one actuator, the at least one suspension element, and the haptic surface are configured to move laterally with respect to the treadle base.

11. The haptic footswitch of claim 1, wherein the at least one actuator, the at least one suspension element, and the haptic surface are configured to move vertically with respect to the treadle base.

12. The haptic footswitch of claim 1, wherein the at least one actuator is a solenoid.

13. An ophthalmic microsurgical system, comprising:
    a footswitch comprising: a body;
    a treadle configured to rotate relative to the body, the treadle comprising:
    a haptic surface, and
    a treadle base, the treadle base pivotably coupled to the body, the haptic surface supported by and spaced a distance apart from the treadle base and displaceable relative to the treadle base;
    at least one suspension element, the suspension element coupled to the haptic surface and separating the haptic surface and the treadle base;
    at least one actuator actuatable to displace the haptic surface relative to the treadle base in a manner providing haptic feedback to the health care provider, wherein movement of the actuator causes movement of the haptic surface relative to the treadle base; and
    a sensor configured to sense the rotational position of the treadle relative to the body and convey data representative of the position of the treadle; and
    a handpiece having a plurality of functions selectively activated based on the rotational position of the treadle.

14. The ophthalmic microsurgical system of claim 13, wherein the haptic surface is shaped and configured as a substantially planar surface having an outer geometry substantially the same as an outer geometry of the treadle base.

15. The ophthalmic microsurgical system of claim 13, wherein the haptic surface possesses less mass than the treadle base.

16. The ophthalmic microsurgical system of claim 13, wherein the haptic surface spaced the distance apart from the treadle base forms a gap between the haptic surface and the treadle base, the at least one suspension element and the at least one actuator are positioned within the gap.

17. The ophthalmic microsurgical system of claim 13, wherein the at least one actuator is a solenoid.

18. The ophthalmic microsurgical system of claim 13, wherein the at least one suspension element provides haptic feedback through isolated movement of the haptic surface independent of the treadle base.

19. A method of providing haptic feedback by a footswitch to a health care provider during a surgical procedure, comprising: detecting a position of a treadle relative to a body of the footswitch with a sensor, the detected position corresponding to surgical mode controllable by the footswitch;
- generating an actuator command signal based on the detected position of the treadle, the actuator command signal having a haptic feedback profile corresponding to the detected position;
- actuating an actuator in accordance with the actuator command signal to displace a haptic surface of the treadle relative to a treadle base of the treadle to signal to the healthcare provider that the treadle is in the detected position;
- wherein actuating an actuator to displace a haptic surface comprises displacing a suspension element coupled to the haptic surface and disposed between the haptic surface and the treadle base, the suspension element displacing the haptic surface relative to the treadle base.

20. The method of claim 19,
- wherein as the treadle moves through a different detected position, a different actuator command signal having a different haptic feedback profile is provided to the actuator to result in a different actuation that signals the healthcare provider the treadle has moved to a different detected position.

* * * * *